United States Patent [19]
Webb et al.

[11] Patent Number: 5,800,358
[45] Date of Patent: Sep. 1, 1998

[54] UNDERSAMPLED OMNIDIRECTIONAL ULTRASONIC FLOW DETECTOR

[75] Inventors: Peter G. Webb, Menlo Park; Hewlett E. Melton, Jr., Sunnyvale, both of Calif.

[73] Assignee: Hewlett Packard Company, Palo Alto, Calif.

[21] Appl. No.: 828,853

[22] Filed: Mar. 31, 1997

[51] Int. Cl.$^6$ .................................................. A61B 8/00
[52] U.S. Cl. ........................................................ 600/454
[58] Field of Search .............................. 600/465, 454, 600/463

[56] References Cited

U.S. PATENT DOCUMENTS

| | | | |
|---|---|---|---|
| 5,105,818 | 4/1992 | Christian et al. | 600/465 |
| 5,373,848 | 12/1994 | Melton, Jr. et al. | 128/661.09 |
| 5,375,600 | 12/1994 | Melton, Jr. et al. | 128/661.09 |
| 5,453,575 | 9/1995 | O'Donnell et al. | 600/465 |
| 5,454,372 | 10/1995 | Benjamin et al. | 128/661.08 |
| 5,628,322 | 5/1997 | Mine | 600/454 |

*Primary Examiner*—Marvin M. Lateef
*Assistant Examiner*—Maulin Patel
*Attorney, Agent, or Firm*—Thomas X. Li

[57] ABSTRACT

A motion detection scheme is described which periodically sends a plurality of pulsed ultrasonic signals from a transducer to a particular range cell to receive a series of backscattered signals from the particular range cell. The time interval between any two pulses is greater than a largest dimension of the range cell divided by a slowest velocity of motion at the particular range cell. A temporal variation between the envelopes of the signals is then determined to detect motion at the particular range cell. This scheme may be applied at all points in an image, to produce images that depict regions undergoing motion.

20 Claims, 4 Drawing Sheets

UNDERSAMPLED OMNIDIRECTIONAL ULTRASONIC FLOW DETECTOR

BACKGROUND OF THE INVENTION

1. Field of the Invention

The present invention pertains to ultrasonic motion detection. More particularly, this invention relates to an undersampled omnidirectional ultrasonic flow detector that has a sampling rate independent of Doppler shift frequency, and a detection sensitivity independent of the direction of the motion relative to the propagation direction of the ultrasound.

2. Description of the Related Art

The measurement of blood flow is a well-known technique for diagnosing diseases. There are, consequently, many different devices and methods for determining blood flow.

One common sensing technique uses ultrasound. In this technique, ultrasound is directed into the patient's body using a transducer. Tiny particles suspended in the blood, such as red blood cells, scatter ultrasound back towards the transducer. The transducer then converts the backscattered ultrasonic energy into an electrical signal that is processed to estimate the velocity of flow.

One prior art motion detection scheme using ultrasound is referred to as Doppler ultrasound. Another prior art motion detection scheme using ultrasound is referred to as color flow imaging. These schemes and their variations (e.g., pulse wave or continuous wave Doppler, Duplex scanning, etc.) estimate blood flow velocities by measuring the phase shift or frequency shift of the backscattered ultrasound signal relative to the transmitted phase or frequency. In essence, these schemes and their variations rely on the Doppler shift for flow detection. The Doppler frequency shift for a particular flow can be calculated from the Doppler equation $$f_d = 2 \cdot (v/c) \cdot f_0 \cdot \cos \theta,$$

where $f_0$ is the frequency of the ultrasonic wave sent into the body, v is the flow velocity, c is the speed of sound, $\theta$ is the angle between the line-of-sight direction of the beam and the flow, and $f_d$ is the detected frequency shift of the signal that returns to the transducer. As long as $\cos\theta$ is not equal to zero, the frequency shift will increase with increasing flow velocity.

The prior art Doppler methods all use the same basic scheme. An ultrasonic pulse is generated by the transducer, and travels along a direction of propagation into the body. At every depth, some fraction of the ultrasound is reflected or backscattered towards the transducer. The signal received after a single ultrasonic pulse thus contains information from all so-called range cells (i.e., the insonated or interrogated regions) along the direction of propagation, separated by the increasing time taken for the echo to return to the transducer from the deeper range cells. The size of the range cells along the propagation direction is determined by the length of the ultrasonic pulse; the size in the orthogonal directions is determined by the spatial extent of the pulse. Note that for any particular range cell, only one sample can be obtained from each ultrasonic pulse. Hence, to measure a velocity or flow at a particular range cell, repeated pulses directed to that range cell are required so that a sufficient number of samples can be obtained to permit an estimate of the phase or frequency shift to be made. Since information from all range cells along the direction of propagation is obtained in each signal, the repeated pulses described here can be processed to provide velocity information at all range cells along this direction.

If flow information is required from many directions, then pulses must be sent in these directions. This can be accomplished either by sending a sequence of pulses in a first direction, then a sequence of pulses in a second direction, and so on, or by interleaving the pulses in all the required directions.

Disadvantages are associated with these prior art Doppler schemes. One disadvantage arises from the repeated ultrasound pulses that are needed to allow measurement of the Doppler shift. Because a frequency or phase measurement is being made, samples from the range cell of interest must be obtained at or above the Nyquist rate; the sampling rate must exceed twice the expected maximum frequency shift. Because only one sample from a particular range cell is obtained from each pulse, the time interval between any two pulses is required to be relatively short. If this constraint is not met, aliasing occurs, and distinct speeds of motion become indistinguishable. This time interval requirement is referred to as sampling rate requirement.

The sampling rate requirement typically causes problems when velocity in an entire image is to be measured simultaneously, since it takes substantial time to direct a pulse along each of the scan lines that make up the entire image. Typically, multiple pulses must be directed in one direction, then a second direction, and so on, to exceed the Nyquist rate. This restricts the frame rate, or the field of view, or the range of Doppler shifts that can be measured, or the accuracy of frequency measurement. This thus requires the ultrasonic imaging system to compromise at least one of these parameters.

Another disadvantage is that the phase shift or frequency shift of the scattered ultrasound is proportional only to the velocity of the flow along the propagation direction of the ultrasonic beam. As can be seen from the above equation, it is not possible to detect any frequency shift if $\theta$ equals 90°, that is, if the flow is perpendicular to the direction of propagation of the ultrasound, regardless of how fast the blood is flowing. Thus, the phase shift or frequency shift is insensitive to motions across the image at a constant distance from the transducer or through the plane of the image.

Many prior proposals have been made to solve or ameliorate the angle dependency and sampling rate limitations of the various prior art Doppler ultrasound schemes. These prior proposals, however, either still require the sampling rate to be higher than the highest expected Doppler shift frequency, or are completely unable to detect motion through the plane of the images.

SUMMARY OF THE INVENTION

One feature of the present invention is the ability to detect motion when the interval between reception of backscattered signals from the range cell of interest is arbitrarily long, thus making such motion detection independent of the Doppler shift frequency of the backscattered signals.

Another feature of the present invention is to allow the sensitivity of ultrasonic motion detection to be independent of the direction of the motion relative to the propagation direction of the ultrasonic beam.

Described below is a motion detection scheme that periodically sends a series of ultrasonic pulses along a particular direction of propagation, and receives a series of backscattered signals from all depths along that direction. Each backscattered signal is sampled by a processor, producing samples from all range cells along the direction of propagation.

To detect motion at one range cell, a single sample from each backscattered signal that corresponds to that range cell is retained, thus forming a new signal. The time interval between acquisition of any two samples in this new signal is determined by the rate at which pulses are transmitted. The processor then determines the temporal variation between the envelopes of the samples to detect motion at that range cell.

To detect motion at all range cells, all samples from all backscattered signals are retained, and reordered so as to produce new signals from all range cells along the direction of propagation. Each new signal includes one sample from each of the series of backscattered signals received by the transducer. The temporal variation between the envelopes of the samples in each of these new signals is determined by the processor, and used to detect motion at all range cells along the direction of propagation.

Further, to produce an image of detected motion, ultrasonic pulses may be sequentially directed in a number of directions, so as to provide samples from all range cells along these directions. In this case, the samples must be reordered to produce new signals from all range cells along each of the directions of propagation. Each new signal includes one sample from each of the pulses directed along the corresponding direction. Once again, the processor measures the temporal variation between the envelopes of the samples in each of these new signals to detect motion at all range cells along each direction of propagation. This produces an image of the detected motion. The pulses may be directed along the various directions in sequence, or in an interleaved fashion as described above.

The envelope signal is used to prevent artifacts due to Doppler shifts, such as would arise if RF or quadrature demodulated signals were used.

Other features and advantages of the present invention will become apparent from the following detailed description, taken in conjunction with the accompanying drawings, illustrating by way of example the principles of the invention.

DETAILED DESCRIPTION OF THE INVENTION

Figure 1:
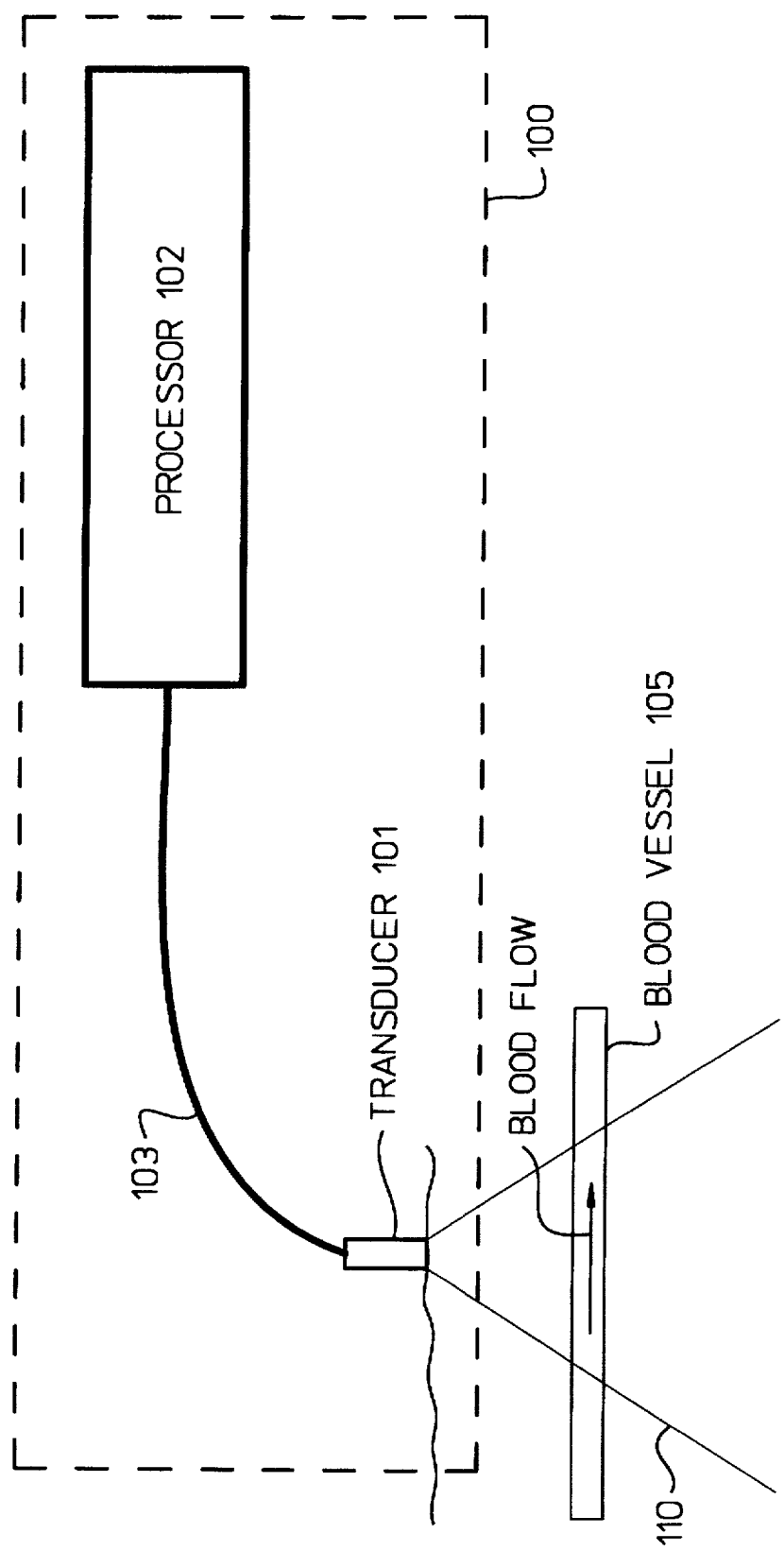
FIG. 1 is a block diagram of an ultrasonic flow motion detector that includes a processor that implements one embodiment of the present invention.

FIG. 1 illustrates a flow motion detector 100 that implements one embodiment of the present invention. As will be described in more detail below, the flow motion detector 100 repeatedly sends ultrasonic pulses to a plurality of range cells and receives backscattered signals from those range cells. The flow motion detector 100 then detects variation between successive samples of the backscattered signals that correspond to each particular range cell. The time interval between any two successive samples can be arbitrarily long, and is not constrained by the maximum Doppler shift. This means that the rate at which the ultrasonic pulses are sent to any particular range cell can be low and is also not constrained by the maximum Doppler shift. By detecting variation, the flow motion detector 100 is able to detect motion regardless of the velocity and direction of the motion relative to the ultrasonic pulses. This can be understood by the following description.

The value of a sample of a backscattered signal is determined by the configuration of scatterers in a range cell at the time that the ultrasonic detection pulse encounters that cell. A backscattered signal is not a simple reflection, but the result of interference between reflections from many individual scatterers that may either cancel or reinforce each other. If no motion is present in the range cell, then no scatterer is replaced in the range cell, and the configuration of scatterers in the range cell remains the same. In this case, the samples from backscattered signals that correspond to this range cell remain constant, and hence the variation between the samples is zero or very small. If, instead, sufficient motion in any direction is present such that all of the scatterers in the range cell are replaced, the configuration of scatterers in the range cell is completely changed. In this case, the expected value of the sample-to-sample variation is large. No further increase in variation is possible by further increasing the velocity. By measuring the sample-to-sample variation at all desired range cells, an image representing the motion at all these range cells can be generated.

As can be seen from the above, the time interval between any two successive samples from a particular range cell determines the velocity of the motion that can be detected at that range cell. The longer the time interval, the slower the motion can be detected. Once the time interval is greater than the largest dimension of the range cell, divided by a slowest velocity of interest, all motion will be equally detected. This condition is referred to as the under-sampling requirement, in contrast to the over-sampling requirement of prior art Doppler ultrasound schemes.

As can be seen from FIG. 1, the flow motion detector 100 includes a transducer 101 and a processor 102. The transducer 101 is used to repeatedly generate and transmit ultrasonic pulses to the range cells 110 of interest and to receive the backscattered signals from the range cells 110. The transducer 101 can be implemented by any known transducer for an ultrasound imaging system. For example, the transducer 101 can be an HP Model 21255B linear array transducer manufactured and sold by Hewlett-Packard Co. of Palo Alto, Calif.

The processor 102 is used to sample the backscattered signals. The processor 102 also processes the samples to determine the variation of the samples of the backscattered signals from each of the range cells 110, in order to detect and display motion. In accordance with one embodiment of the present invention, the pulses are sent to each range cell at a sufficiently low rate R that complete replacement of scatterers in the range cell occurs if motion above some threshold velocity is present at that range cell. This rate is not constrained by the sampling requirement imposed by the maximum Doppler shift. This allows the time interval between any two successive samples from any particular range cell to be very long in comparison to that required by prior art Doppler motion detectors.

Using a sample rate lower than the rate R allows the motion detection to be insensitive to the velocity and direction of the motion. As described above, we refer to this condition as the under-sampling requirement. The under-sampling requirement can be expressed as follows:

$$R < V_{slowest}/d_{largest}$$

where $d_{largest}$ represents the largest dimension of the range cell, and $V_{slowest}$ represents the slowest velocity of interest.

After sampling, the processor 102 computes the envelope signal of each sampled backscattered signal. Alternatively, the envelope can be computed by an analog circuit before the signals are sampled. The processor 102 then calculates or computes the temporal variation in the amplitude between the samples of the envelope signals that correspond to each range cell of interest. As described above, the amplitude of each envelope signal depends on the configuration of scatterers in the range cell. If no motion is present, no scatterers are replaced in the range cell and the configuration of scatterers in the range cell remains the same. In this case, the samples of the envelope signals will be equal to one another, and the variation is equal to zero. If sufficient motion in any direction is present in the range cell such that all of the scatterers in the range cell are replaced, the expected value of the variation will rise to a maximum value determined by the detailed nature of the scatterers in the range cell, regardless of the direction of the motion. The maximum value will remain the same, despite increases in the temporal spacing. If the motion replaces only some fraction of the scatterers, then some variation value that is intermediate between zero and the maximum value will be observed. Thus, by using such variation, motion can be detected at arbitrarily low sample rates that are independent of the Doppler shift frequency of the backscattered signals. In addition, the detection sensitivity is independent of the direction of motion with respect to the direction of the detection beam because the detection is not based on the detection of the Doppler shift.

The temporal variation between the envelope signals is a function of the distance moved by the scatterers between images, as well as the size of the range cell. Once the velocity is sufficient that an entirely new set of scatterers fills the range cell between acquisitions, the motion detection of the flow motion detector 100 becomes insensitive to further variation, and thus results in a robust indication of motion.

The processor 102 can calculate the temporal variation v using different equations. In accordance with one embodiment, the processor 102 calculates the temporal variation v at a range cell (x,y) by calculating the root mean square (RMS) difference between sequential envelope signals at that range cell (x,y). The difference is then normalized by the RMS value of the envelope signal. That is, at a spatial range cell (x,y), the temporal variation v is calculated as follows:

$$v_{RMS}(x, y) = \sqrt{\left\{ \sum_{m=1}^{n-1} [(S_{m+1}(x, y) - S_m(x, y))^2] \right\} / (n-1)} / \sqrt{\left\{ \sum_{m=1}^{n} S_m^2(x, y) \right\} / n},$$

where $s_m(x,y)$ represents the sample of the envelope signal obtained from range cell (x,y) at time m, and n represents some number of samples of envelope signals corresponding to the range cell.

In order to overcome noise and other interferences that may occur to the envelope signals, and in order to ensure true motion detection, a threshold value greater than zero is set for the temporal variation. This means that motion is detected once it causes the temporal variation to exceed the threshold value. Experiments and/or statistical analysis can be used to determine an appropriate threshold value.

In one embodiment, a threshold value corresponding to a flow velocity of two centimeters per second proved appropriate. In alternative embodiments, the threshold value might be greater or less than this value.

To enhance motion detection, an ultrasonic contrast agent can be used in conjunction with the flow motion detector 100. The ultrasonic contrast agent preferentially increases the backscattered signal from blood. This can enhance the ability of the processor 102 of the flow motion detector 100 to detect slow flow, to reject small changes in static tissues, and to reject noise. The effects of the contrast agent can also be amplified by having the processor 102 receive and process the second or higher harmonic signals that such an agent may generate.

The processor 102 may also employ other schemes for calculating the temporal variation v. The most desirable calculation may depend on the nature of the interference signals that produce spurious reports of motion. If the interference is primarily thermal noise, which we expect to have a Gaussian distribution, then the above described equation is preferred. If, on the other hand, background tissue motion produces occasional large contributions to the temporal variation v, then the following equations might be more effective. They are $$v_{ABS}(x, y) = \left\{ \sum_{m=1}^{n-1} |S_{m+1}(x, y) - S_m(x, y)| \right\} / (n-1) / \sqrt{\left\{ \sum_{m=1}^{n} S_m^2(x, y) \right\} / n},$$

and $$v_{MEDIAN}(x, y) = MEDIAN|S_{m+1}(x, y) - S_m(x, y)| / \sqrt{\left\{ \sum_{m=1}^{n} S_m^2(x, y) \right\} / n}.$$

The $v_{ABS}(x,y)$ calculation provides greater emphasis on smaller variations and the $v_{MEDIAN}(x,y)$ calculation will not be affected by the value of a few large deviations.

In addition, all of the above described variation calculations use root-mean-square normalization. The normalization can be changed depending on the nature of the image. If there are substantial bright structures representing slowly moving tissue that should not be displayed as moving, then mean normalization is preferred. If there are image voids with very low mean values, then mean normalization may amplify variation due to noise or other sources in these range cells. In this case, un-normalized measures may be more effective.

Further, all of the above described equations calculate a variation value at each range cell in the image using a certain length time series of input images. If greater time resolution is required, this may be obtained at the cost of spatial resolution by performing some averaging over spatial regions comprising several range cells, and using shorter time segments.

The processor 102 can also form an entire image representing the motion by repeating this operation at different range delays and for different beam angles, as is done in forming conventional ultrasonic images, and determining the variation at each range cell thus scanned for the image. Range cells at which the temporal variation exceeds the threshold value can then be marked as containing moving material. The order of acquisition of backscattered signals can be such that a set of signals is collected in immediate succession for a particular direction, followed by similar sets of signals for other directions, or an interleaved acquisition order can be used. The latter scheme is compatible with the usual way that ultrasound images are formed, and is thus preferred.

The processor 102 can be implemented by dedicated hardware circuits, software routines, and/or firmware. In one embodiment, the processor 102 is implemented by dedicated hardware circuits. In another embodiment, the processor 102 is implemented by software routines and/or firmware. Alternatively, the processor 102 can be implemented by a combination of hardware and software. The structure of the processor 102 will be described in more detail below, also in conjunction with FIGS. 2–4.

Figure 2:
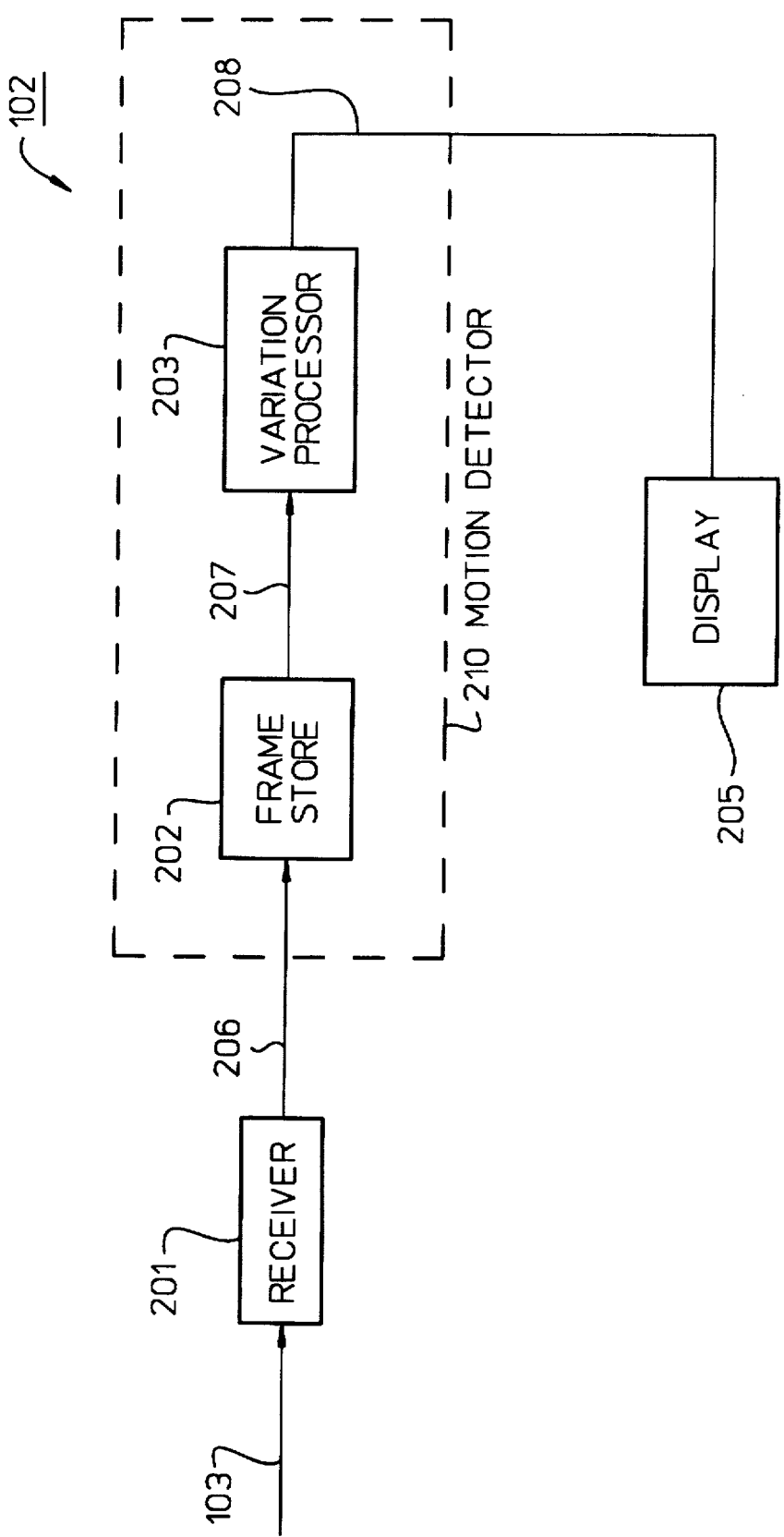
FIG. 2 shows in block diagram form the processor of FIG. 1.

As can be seen from FIG. 2, the processor 102 includes a receiver 201 that is connected to the transducer 101 (FIG. 1) via signal line 103. The receiver 201 is also connected to a frame store 202. The frame store 202 is then connected to a variation processor 203. The variation processor 203 is then connected to a display 205. The frame store 202 and the variation processor 203 form a motion detector 210.

The receiver 201 receives the backscattered signals from the transducer 101 via the signal line 103. The receiver 201 is used to process the received backscattered signals into the envelope signals. The signal processing functions of the receiver 201 may include demodulation, integration, and sampling. These processing functions of the receiver 201 can be done using known means.

The receiver 201 then computes the envelope signal for each of the backscattered signals. Alternatively, an analog circuit can be used to calculate the envelope signal prior to the sampling function of the processor.

One envelope signal from each of the desired directions is used to form an image frame, which, after scan conversion, is displayed on the display 205.

Figure 3:
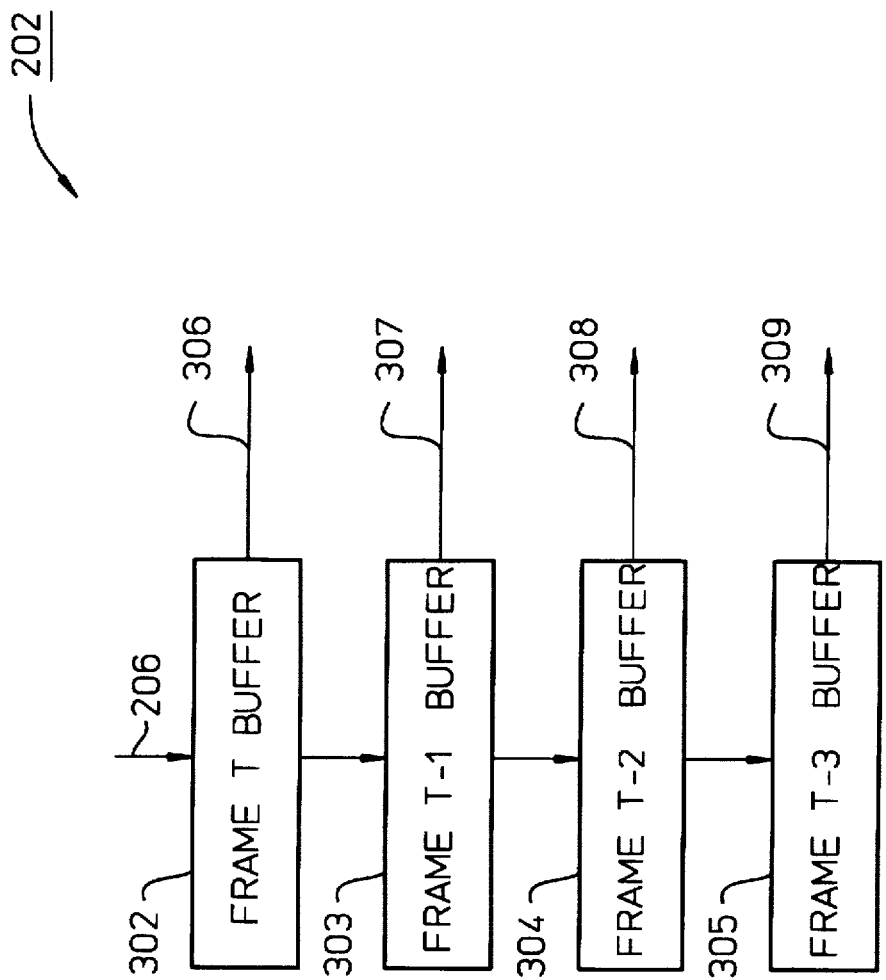
FIG. 3 shows the functional structure of a frame store of the processor of FIG. 2.

As the backscattered signals are sequentially received in the receiver 201, their envelope signals (and thus the image frames) are also sequentially computed. The computed image frames are then stored in the frame store 202. The frame store 202 can be implemented by any storage device. In one embodiment, the frame store 202 stores the image frames in a first-in-first-out (FIFO) manner. This means that the frame store 202 only stores the most recent image frames. The number of image frames retained in the frame store 202 depends on the storage space in the frame store 202. FIG. 3 shows the structure of the frame store 202.

As can be seen from FIG. 3, the frame store 202 includes a number of frame buffers 302 through 305. When a first image frame is received from the receiver 201 (FIG. 2), the image is stored in the frame T buffer 302. When a new image frame is received from the receiver 202, the existing image frame stored in the frame T buffer 302 is pushed to the frame T-1 buffer 303 and the new image frame is stored in the frame T buffer 302. In other words, the frame T buffer 302 always stores the most recent image frame received from the receiver 202 and the frame T-3 buffer 305 stores the least recent image frame received from the receiver 202.

Figure 4:
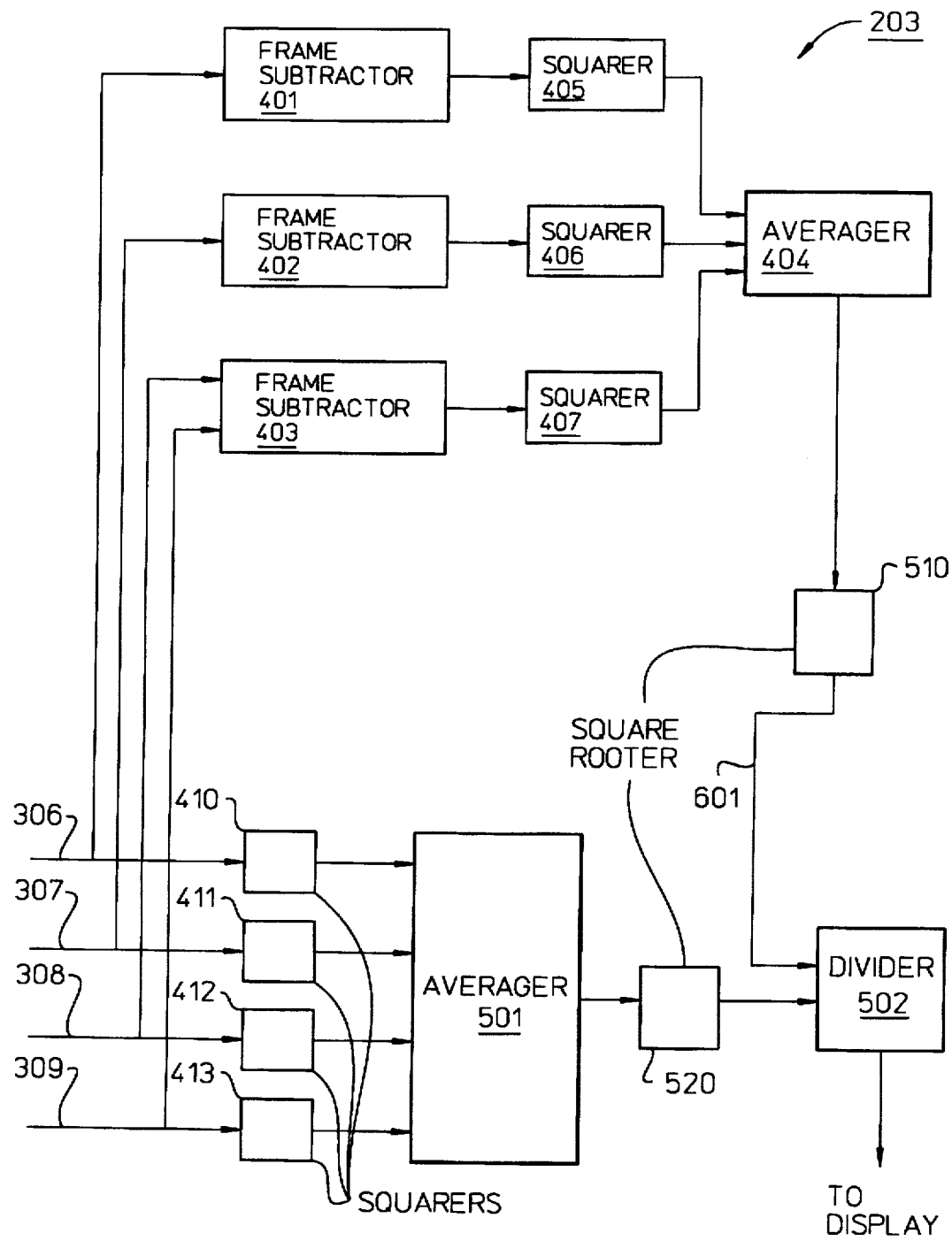
FIG. 4 shows the functional structure of the variation processor of FIG. 2.

In one embodiment and as can be seen from FIG. 3, the frame store 202 includes four frame buffers 302–305. Alternatively, more or fewer frame buffers may be included in the frame store 202. As also can be seen from FIG. 3, each of the frame buffers 302–305 includes an output that is connected to the variation processor 203 (FIG. 2) for the calculation of the variation at each range cell of interest. FIG. 4 shows the structure of the variation processor 203, which will be described in more detail below.

In FIG. 4, the variation processor 203 includes frame subtractors 401 through 403, squarers 405–407 and an averager 404. The variation processor 203 also includes squarers 410–413 and an averager 501. Further, the variation processor 203 includes square rooters 510 and 520 and divider 502. Each of the frame subtractors 401–403 receives two image frames from the frame store 202. For example, the frame subtractor 401 receives the image frames stored in the frame buffers 304 and 305 (FIG. 3) and the frame subtractor 403 receives the image frames from the frame buffers 302 and 303 (FIG. 3). Each of the subtractors 401–403 subtracts one image frame from a subsequent image frame. The results of each of these subtraction operations are squared by the squarers 405–407 and are averaged together by the averager 404. The square root is then calculated by square rooter 510. The square rooter 510 then sends its output to the divider 502. It is to be noted that the operations specified are carried out at each pixel in the image frames.

The squarers 410–413 receive the image frames from the frame store 202. Their outputs are sent to the averager 501. The averager 501 then averages all the image frames, and the square root is taken by square rooter 520. The result is then applied to the divider 502 to be used by the divider 502 to divide the output of square rooter 510.

Each of the frame subtractors 401–403 can be implemented by any known subtraction circuit or software routine. In addition, the averager 404 and the squarers 405–407 and 410–413, the square rooters 510 and 520, and the divider 502 can also be implemented by any known circuit or software routine.

In the foregoing specification, the invention has been described with reference to specific embodiments thereof. It will, however, be evident to those skilled in the art that various modifications and changes may be made thereto without departing from the broader spirit and scope of the invention. The specification and drawings are, accordingly, to be regarded in an illustrative rather than a restrictive sense.

What is claimed is:

1. A motion detection method, comprising the steps of:

(A) sending a sequence of pulsed ultrasonic signals from an ultrasonic transducer to a particular range cell (x,y) to generate a sequence of backscattered signals from that range cell, wherein time interval between any successive pulsed ultrasonic signals is not constrained by maximum Doppler shift;

(B) determining temporal variation (v) between envelops of the backscattered signals to detect motion at the range cell regardless of velocity and direction of the motion relative to the pulsed ultrasonic signals.

2. The motion detection method of claim 1, wherein the pulsed ultrasonic signals are separated by a time interval greater than the largest dimension of the range cell divided by the slowest velocity of interest.

3. The motion detection method of claim 1, wherein motion at the range cell is detected when the temporal variation (v) exceeds a predetermined value.

4. The motion detection method of claim 2, further comprising (I) receiving the backscattered signals from a multiplicity of range cells along the direction of propagation of the pulsed ultrasound signals;

(II) determining the temporal variation between envelops of the backscattered signals corresponding to each of the range cells to detect motion at all of the range cells.

5. The motion detection method of claim 2, further comprising (I) transmitting a plurality of sequences of ultrasonic pulses to a plurality of range cells not all in a single direction of propagation to receive their respective backscattered signals, the plurality of sequences of ultrasonic pulses to any particular range cell may be interleaved or sequentially transmitted;

(ii) determining the temporal variation between envelopes of the backscattered signals corresponding to each of the range cells to detect motion at all of the range cells.

6. The motion detection method of claim 1, wherein the temporal variation is determined by calculating an estimate of a root mean square variation of the envelopes of the backscattered signals.

7. The motion detection method of claim 6, wherein the temporal variation (v) is determined in accordance with the equation $$v(x, y) = \sqrt{\left\{\sum_{m=1}^{n-1}[(S_{m+1}(x, y) - S_m(x, y))]^2\right\}/(n-1)} / \sqrt{\left\{\sum_{m=1}^{n}S_m^2(x, y)\right\}/n},$$

wherein s represents the envelope value of one sample and n represents the total number of backscattered signals.

8. The motion detection method of claim 1, wherein the temporal variation (v) is determined in accordance with the following equation $$V(x, y) = \text{MEDIAN}|S_{m+1}(x, y) - S_m(x, y)|/\sqrt{\left\{\sum_{m=1}^{n}S_m^2(x, y)\right\}/n},$$

wherein s represents the envelope value of one sample and n represents the total number of backscattered signals.

9. The motion detection method of claim 1, wherein the temporal variation (v) is determined in accordance with the following equation $$v(x, y) = \left\{\sum_{m=1}^{n-1}|S_{m+1}(x, y) - S_m(x, y)|\right\}/(n-1) / \sqrt{\left\{\sum_{m=1}^{n}S_m^2(x, y)\right\}/n},$$

wherein s represents the envelope value of one sample and n represents the total number of backscattered signals.

10. The motion detection method of claim 1, wherein the particular range cell is within a blood vessel or organ.

11. The motion detection method of claim 2, wherein the time interval is independent of Doppler shift frequency of the backscattered signals.

12. An ultrasonic motion detector, comprising:

(A) a transducer that periodically sends a sequence of pulsed ultrasonic signals to a particular range cell (x,y) and receives a sequence of backscattered signals from the range cell, wherein time interval between any successive pulsed ultrasonic signals is not constrained by maximum Doppler shift;

(B) a processor is coupled to the transducer to determine temporal variation (v) between envelops of samples of the backscattered signals to detect motion at the range cell regardless of velocity and direction of the motion relative to the pulsed ultrasonic signals.

13. The ultrasonic motion detector of claim 12, wherein the pulsed ultrasonic signals are separated by a time interval greater than the largest dimension of the range cell divided by the slowest velocity of interest.

14. The ultrasonic motion detector of claim 13, wherein the processor further comprises (a) a receiver coupled to the transducer to (1) sample the received back-scattered signals and (2) convert each of the sampled back-scattered signals into a respective one of a series of image frames;

(b) a frame store coupled to the receiver to store the image frames;

(c) a variation processor coupled to the frame store to calculate the temporal variation.

15. The ultrasonic motion detector of claim 14, wherein the variation processor determines the temporal variation (v) by calculating an estimate of a root mean square variation of the sampled back-scattered signals.

16. The ultrasonic motion detector of claim 15, wherein the variation processor determines the temporal variation (v) in accordance with the following equation $$v(x, y) = \sqrt{\left\{\sum_{m=1}^{n-1}[(S_{m+1}(x, y) - S_m(x, y))]^2\right\}/(n-1)} / \sqrt{\left\{\sum_{m=1}^{n}S_m^2(x, y)\right\}/n},$$

wherein s represents the envelope value of one sample and n represents the total number of backscattered signals.

17. The ultrasonic motion detector of claim 14, wherein the variation processor determines the temporal variation (v) in accordance with the following equation $$V(x, y) = \text{MEDIAN}|S_{m+1}(x, y) - S_m(x, y)|/\sqrt{\left\{\sum_{m=1}^{n}S_m^2(x, y)\right\}/n},$$

wherein s represents the envelope value of one sample and n represents the total number of backscattered signals.

18. The ultrasonic motion detector of claim 14, wherein the variation processor determines the temporal variation (v) in accordance with the following equation $$v(x, y) = \left\{\sum_{m=1}^{n-1}|S_{m+1}(x, y) - S_m(x, y)|\right\}/(n-1) / \sqrt{\left\{\sum_{m=1}^{n}S_m^2(x, y)\right\}/n},$$

wherein s represents the envelope value of one sample and n represents the total number of backscattered signals.

19. The ultrasonic motion detector of claim 12, wherein the particular range cell is within a blood vessel or organ.

20. The ultrasonic motion detector of claim 13, wherein the time interval is independent of Doppler shift frequency of the received back scattered signals.

* * * * *